United States Patent
Nakai et al.

(10) Patent No.: US 11,524,099 B2
(45) Date of Patent: Dec. 13, 2022

(54) COMPOSITION FOR ACOUSTIC WAVE PROBE, SILICONE RESIN FOR ACOUSTIC WAVE PROBE USING THE SAME, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

(71) Applicant: FUJIFILM Corporation, Tokyo (JP)

(72) Inventors: Yoshihiro Nakai, Kanagawa (JP); Takayasu Nagai, Kanagawa (JP); Atsushi Osawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 1342 days.

(21) Appl. No.: 15/831,774

(22) Filed: Dec. 5, 2017

(65) Prior Publication Data

US 2018/0104384 A1 Apr. 19, 2018

Related U.S. Application Data

(63) Continuation of application No. PCT/JP2016/068964, filed on Jun. 27, 2016.

(30) Foreign Application Priority Data

Jun. 30, 2015 (JP) ............... JP2015-132100

(51) Int. Cl.
*A61B 8/00* (2006.01)
*C08K 3/22* (2006.01)
*C08L 83/04* (2006.01)
*A61L 31/06* (2006.01)
*H04R 19/00* (2006.01)
*C08G 77/12* (2006.01)
*C08G 77/20* (2006.01)
*C08G 77/00* (2006.01)
*G10K 11/30* (2006.01)
*B06B 1/06* (2006.01)
*G10K 11/02* (2006.01)
*A61B 5/00* (2006.01)

(52) U.S. Cl.
CPC ............ *A61L 31/06* (2013.01); *A61B 5/0095* (2013.01); *B06B 1/067* (2013.01); *C08G 77/12* (2013.01); *C08G 77/20* (2013.01); *C08G 77/80* (2013.01); *C08L 83/04* (2013.01); *G10K 11/02* (2013.01); *G10K 11/30* (2013.01); *H04R 19/00* (2013.01); *A61B 8/4281* (2013.01); *A61B 8/44* (2013.01); *C08K 2003/2296* (2013.01)

(58) Field of Classification Search
None
See application file for complete search history.

(56) References Cited

U.S. PATENT DOCUMENTS

| | | | |
|---|---|---|---|
| 4,901,729 A | 2/1990 | Saitoh et al. | |
| 5,079,300 A | 7/1992 | Dubrow et al. | |
| 2005/0070801 A1 | 3/2005 | Yamashita et al. | |
| 2007/0282204 A1* | 12/2007 | Yamashita | G10K 11/02 600/459 |
| 2009/0069486 A1 | 3/2009 | Yamashita et al. | |
| 2009/0243436 A1 | 10/2009 | Rubinsztajn et al. | |
| 2015/0299543 A1* | 10/2015 | Miyamoto | C08K 3/26 524/588 |
| 2016/0185912 A1* | 6/2016 | Mizunashi | C08L 83/04 428/220 |

FOREIGN PATENT DOCUMENTS

| | | |
|---|---|---|
| EP | 1 519 362 A2 | 3/2005 |
| EP | 2 930 213 A1 | 10/2015 |
| EP | 3 124 545 A1 | 2/2017 |
| JP | 63-220847 A | 9/1988 |
| JP | 04-503825 A | 7/1992 |
| JP | 2000-080280 A | 3/2000 |
| JP | 2004-305339 A | 11/2004 |
| JP | 2005-125071 A | 5/2005 |
| JP | 2011-072702 A | 4/2011 |
| JP | 2012-034160 A | 2/2012 |
| JP | 2014-188009 A | 10/2014 |
| WO | 2014/088115 A1 | 6/2014 |
| WO | 2014/200112 A1 | 12/2014 |

OTHER PUBLICATIONS

Communication dated Jun. 26, 2018, from the Japanese Patent Office in counterpart application No. 2017-526333.
International Search Report dated Aug. 30, 2016 in counterpart international application No. PCT/JP2016/068964.
International Preliminary Report on Patentability dated Jan. 2, 2018 in counterpart international application No. PCT/JP2016/068964.
Written Opinion of the International Searching Authority dated Aug. 30, 2016 in counterpart international application No. PCT/JP2016/068964.
Communication dated Sep. 18, 2018 from the Japanese Patent Office in counterpart application No. 2017-526333.
Communication, dated Aug. 30, 2018, issued in corresponding EP Application No. 16817854.9, 9 pages in English.
Notice of Reasons for Refusal dated Oct. 15, 2019 issued by the Japanese Patent Office in corresponding Application No. 2018-235788.

* cited by examiner

*Primary Examiner* — David J Buttner
(74) *Attorney, Agent, or Firm* — Sughrue Mion, PLLC

(57) ABSTRACT

Provided is a composition for an acoustic wave probe including a polysiloxane mixture containing at least polysiloxane having a vinyl group and a phenyl group, polysiloxane having two or more Si—H groups in a molecular chain, and zinc oxide, a silicone resin for an acoustic wave probe, the acoustic wave probe, an acoustic wave measurement apparatus, an ultrasound diagnostic apparatus, an ultrasound probe, a photoacoustic wave measurement apparatus, and an ultrasound endoscope.

5 Claims, 1 Drawing Sheet

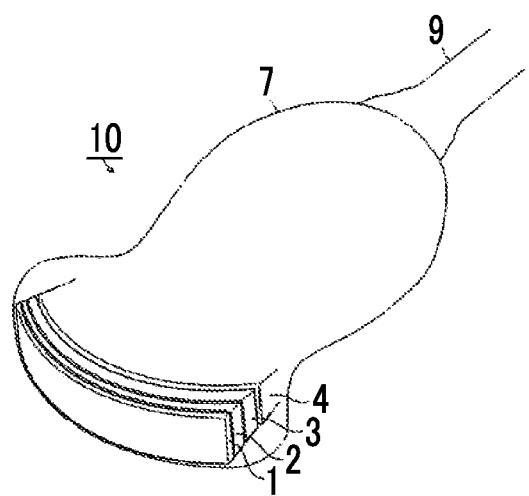

COMPOSITION FOR ACOUSTIC WAVE PROBE, SILICONE RESIN FOR ACOUSTIC WAVE PROBE USING THE SAME, ACOUSTIC WAVE PROBE, ULTRASOUND PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

CROSS-REFERENCE TO RELATED APPLICATIONS

This application is a Continuation of PCT International Application No. PCT/JP2016/068964 filed on Jun. 27, 2016, which claims priority under 35 U.S.C. § 119(a) to Japanese Patent Application No. 2015-132100 filed in Japan on Jun. 30, 2015. Each of the above applications is hereby expressly incorporated by reference, in its entirety, into the present application.

BACKGROUND OF THE INVENTION

1. Field of the invention

The present invention relates to a composition for an acoustic wave probe, a silicone resin for an acoustic wave probe using the same, the acoustic wave probe, and an ultrasound probe. Furthermore, the present invention relates to an acoustic wave measurement apparatus, an ultrasound diagnosis, apparatus, a photoacoustic wave measurement apparatus, and an ultrasound endoscope.

2. Description of the Related Art

In the acoustic wave measurement apparatus, an acoustic wave probe is used which irradiates a test object with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

An acoustic wave having an appropriate frequency in accordance with a test object, measurement conditions, and the like from an ultrasonic wave or a photoacoustic wave is selected as the acoustic wave.

For example, the ultrasound diagnostic apparatus transmits an ultrasonic wave to the interior of a test object, receives the ultrasonic wave reflected by the tissues inside the test object, and displays the received ultrasonic wave as an image. The photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

The acoustic wave measurement apparatus performs transmission and reception of an acoustic wave on a living body (typically, the human body) which is a test object. Therefore, it is necessary to fulfil requirements such as consistency in the acoustic impedance within the living body and decrease in acoustic attenuation.

For example, a probe for an ultrasound diagnostic apparatus (also referred to as an ultrasound probe) which is a kind of acoustic wave probe includes a piezoelectric element which transmits and receives an ultrasonic wave and an acoustic lens which is a portion coming into contact with a living body. An ultrasonic wave generated from the piezoelectric element is incident on the living body after being transmitted through the acoustic lens. In a case where the difference between acoustic impedance (density x acoustic velocity) of the acoustic lens and acoustic impedance of the living body is large, the ultrasonic wave is reflected b the surface of the living body, and therefore, is not efficiently incident on the living body. For this reason, it is difficult to obtain favorable resolution. In addition, it is desirable that ultrasonic attenuation of the acoustic lens is low in order to transmit and receive the ultrasonic wave with high sensitivity.

For this reason, a silicone resin of which the acoustic impedance is close to the acoustic impedance (in the case of the human body, $1.4 \times 10^6$ to $1.7 \times 10^6$ kg/m$^2$/sec) of a living body and which ahs a low ultrasonic attenuation is used as a material of the acoustic lens.

An acoustic lens composition containing silicone rubber and zinc oxide powder is disclosed, for example, in JP2005-125071A, as a composition for an acoustic lens. In addition, a technique relating to ultrasound propagation medium made of synthetic rubber which is a sulfurated type by adding at least peroxide is disclosed in JP1988-220847A (JP-S63-220847A).

SUMMARY OF THE INVENTION

A silicone resin alone is soft and has a low mechanical strength. For this reason, inorganic filler (also referred to as inorganic filling agent) is formulated in a composition for forming the silicone resin as shown in JP2005-125071A for the purpose of improving hardness and the mechanical strength. In addition, in some cases, zinc oxide may be added in order to make acoustic impedance of an ultrasound propagation medium be close to acoustic impedance of a test object as shown in JP1988-220847A (JP-S63-220847A).

However, the silicone resin formed of the composition disclosed in JP2005-125071A and the ultrasound propagation medium disclosed in JP1988-220847A (JP-S63-220847A) have low abrasion resistance. In the silicone resin prepared from the acoustic lens composition disclosed in JP2005-125071A and the ultrasound propagation medium disclosed in JP1988-220847A (JP-S63-220847A), it is difficult to satisfy all conditions such as resin hardness, abrasion resistance, and reduced acoustic attenuation, which are required for an acoustic wave probe, to a high level.

The present invention has been made in consideration of the above-described circumstances, and an object of the present invention is to provide a composition for an acoustic wave probe in which acoustic impedance is close to a value of a living body and acoustic attenuation reduces, and which can effectively improve the hardness and the mechanical strength (tear strength and abrasion resistance) of a silicone resin, a silicone resin for an acoustic wave probe using the same, the acoustic wave probe, an ultrasound probe, an acoustic wave measurement apparatus, an ultrasound diagnostic apparatus, a photoacoustic wave measurement apparatus, and an ultrasound endoscope.

In addition, another object of the present invention is to provide a composition for an acoustic wave probe and a silicone resin for an acoustic wave probe in which it is possible to improve the sensitivity of a photoacoustic wave measurement apparatus in which observation of deeper regions of a human-body is difficult due to low sensitivity in the ultrasound probe in which capacitive micromachined ultrasonic transducers (cMUT) are used as ultrasonic diagnostic transducer arrays, the photoacoustic wave measurement apparatus, and the ultrasound endoscope.

The present inventors have conducted extensive studies on inorganic compounds and polysiloxane to be added to a silicone resin. As a result, they have found that a silicone resin prepared using a composition containing zinc oxide and polysiloxane, which contains a specific group, has acoustic impedance close to a value of a living body, has reduced acoustic attenuation, has an excellent hardness and mechanical strength, and can be suitably used in an acoustic wave probe. The present invention has been completed based on this finding.

The above-described problems are solved by the following means.

<1> A composition for an acoustic wave probe, comprising: a polysiloxane mixture containing at least polysiloxane having a vinyl group and a phenyl group, polysiloxane having two or more Si—H groups in a molecular chain, and zinc oxide.

<2> The composition for an acoustic wave probe according to <1>, in which 0.1 to 60 parts by mass of the zinc oxide is contained in 100 parts by mass in total of the polysiloxane mixture.

<3> The composition for an acoustic wave probe according to <1> or <2>, in which 10 to 99.6 parts by mass of the polysiloxane having a vinyl group and a phenyl group and 0.4 to 90 parts by mass of the polysiloxane having two or more Si—H groups in a molecular chain are contained in 100 parts by mass in total of the polysiloxane mixture.

<4> The composition for an acoustic wave probe according to any one of <1> to <3>, in which an average primary particle diameter of the zinc oxide is 10 to 200 nm.

<5> The composition for an acoustic wave probe according to any one of <1> to <4>, in which the zinc oxide is subjected to surface treatment using a silane compound.

<6> The composition for an acoustic wave probe according to any one <1> to <5>, in which a mass average molecular weight of the polysiloxane having a vinyl group and a phenyl group is 10,000 to 200,000.

<7> The composition for an acoustic wave probe according to any one of <1> to <6>, in which a mass average molecular weight of the polysiloxane having a vinyl group and a phenyl group is 30,000 to 150,000.

<8> The composition for an acoustic wave probe according to any one of <1> to <7>, in which a Si—H equivalent of the polysiloxane having two or move Si—H groups in a molecular chain is 50 to 1,300 g/mol.

<9> The composition for an acoustic wave probe according to any one of <1> to <8>, in which the polysiloxane having two or more Si—H groups in a molecular chain has a phenyl group.

<10> The composition for an acoustic wave probe according to any one of <1> to <9>, further comprising: 0.0001 to 0.1 parts by mass of platinum or a platinum-containing compound with respect to 100 parts by mass of the polysiloxane mixture.

<11> A silicone resin for an acoustic wave probe which is obtained by subjecting the composition for an acoustic wave probe according to any one of <1>to <10> to a vulcanization reaction.

<12> An acoustic wave probe comprising: at least one selected from the group consisting of an acoustic lens and an acoustic matching layer which contain the silicone resin for an acoustic wave probe according to <11>.

<13> An ultrasound probe comprising: a capacitive micromachined ultrasonic transducer; and an acoustic lens containing the silicone resin for an acoustic wave probe according to <11>.

<14> An acoustic wave measurement apparatus comprising: the acoustic wave probe according to <12>.

<15> An ultrasound diagnostic apparatus comprising; the acoustic wave probe according to <12>.

<16> A photoacoustic wave measurement apparatus comprising: an acoustic lens containing the silicone resin for an acoustic wave probe according to <11>.

<17> An ultrasound endoscope comprising; an acoustic lens containing the silicone resin for an acoustic wave probe according to <11>.

Unless otherwise specified in the description of the present invention, in a case where there are groups having the same reference numerals as each other in general formulas, these may be the same as or different from each other, and a group (for example, an alkyl group) specified by each group may further be substituted with a substituent.

In addition, "to" in the present invention is used for the meaning of including numerical values described before and after "to" as lower limit values and upper limit values.

Unless otherwise specified, the mass average molecular weight in the present invention refers to a value (in terms of polystyrene) measured through gel permeation chromatography (GPC).

According to the present invention, it is possible to provide a composition for an acoustic wave probe in which acoustic impedance is close to a value of a living body and acoustic (particularly preferably ultrasonic) attenuation reduces, and which can significantly improve the hardness and the mechanical strength (tear strength and abrasion resistance) of a silicone resin, a silicone resin for an acoustic wave probe using the same (hereinafter, also simply referred to as a "silicone resin"), the acoustic wave probe, an acoustic wave measurement apparatus, and an ultrasound diagnostic apparatus.

In addition, it is possible to provide an ultrasound probe in which cMUT is used as an ultrasonic diagnostic transducer array, and the silicone resin for an acoustic wave probe which can improve the sensitivity of the photoacoustic wave measurement apparatus and the ultrasound endoscope.

The above-described characteristics and advantages and other characteristics and advantages of the present invention become clearer in the following descriptions with reference to the accompanying drawing.

BRIEF DESCRIPTION OF THE DRAWING

FIG. 1 is a perspective transparent view of an example of a convex ultrasound probe which is an aspect of an acoustic wave probe.

DESCRIPTION OF THE PREFERRED EMBODIMENTS

<Composition for Acoustic Wave Probe>

A composition for an acoustic wave probe of the present invention (hereinafter, also simply referred to as a "composition") is a composition for an acoustic wave probe containing a polysiloxane mixture containing at least polysiloxane having a vinyl group and a phenyl group, polysiloxane having two or more Si—H groups in a molecular chain, and zinc oxide.

The content of zinc oxide in 100 parts by mass in total of the polysiloxane mixture is not particularly limited, but is preferably 0.1 to 70 parts by mass, more preferably 0.1 to 60 party by mass, still more preferably 5 to 60 parts by mass, and particularly preferably 20 to 50 parts by mass.

in a case where the content of zinc oxide is within the above-described ranges, it is possible to make acoustic impedance be close to a value of the human body, to improve abrasion resistance, and to enhance acoustic sensitivity.

In addition, the content of polysiloxane having a vinyl group and a phenyl group in 100 parts by mass in total of the polysiloxane mixture is preferably 10 to 99.6 parts by mass. The content of polysiloxane having two or more Si—H groups in a molecular chain in 100 parts by mass in total of the polysiloxane mixture is preferably 0.4 to 90 parts by mass and more preferably 0.5 to 70 parts by mass. The content of the polysiloxane having a vinyl group and a phenyl group is more preferably 30 to 80 parts by mass and the content of the polysiloxane having two or more Si—H groups in a molecular chain is more preferably 1 to 50 parts by mass.

The polysiloxane mixture refers to a mixture which does not contain a catalyst for crosslinking and polymerizing the polysiloxane having a vinyl group and a phenyl group and the polysiloxane having two or more Si—H groups in a molecular chain. Accordingly, the polysiloxane mixture contains zinc oxide but no catalyst.

The polysiloxane mixture contains the polysiloxane having a vinyl group and a phenyl group (polyorganosiloxane) (hereinafter, reserved to as a polysiloxane (A) having a vinyl group and a phenyl group) and a polysiloxane having two or more Si—H groups in a molecular chain (hereinafter, referred to as a polysiloxane (B) having two or more Si—H groups in a molecular chain) as described above. However, the polysiloxane (B) having two or more Si—H groups in a molecular chain is preferably a polyorganosiloxane (B) having two or more Si—H groups in a molecular chain.

Accordingly, in the present invention, the polysiloxane mixture preferably contains at least the polysiloxane (A) having a vinyl group and a phenyl group, the polysiloxane (B) having two or more Si—H groups in a molecular chain, and zinc oxide.

In the following detailed description, the polysiloxane (A) having a vinyl group and a phenyl group and the polysiloxane() having two or more Si—H groups in a molecular chain which are preferred aspect will be described. However, the present invention is not limited to the aspects.

<Polysiloxane (A) Having Vinyl Group and Phenyl Group>

The polysiloxane (A) having a vinyl group and a phenyl group (hereinafter, also simply referred to as a polysiloxane (A)) used in the present invention has two or more vinyl groups in a molecular chain.

Examples of the polysiloxane (A) having a vinyl group and a phenyl group include polysiloxane (a) having vinyl groups at least at both terminals of a molecular chain (hereinafter, also simply referred to as polysiloxane (a)) or polysiloxane (b) having at least two —O—Si(CH$_3$)$_2$(CH=CH$_2$) in a molecular chain (hereinafter, also simply referred to as a polysiloxane (b)). Among them, the polysiloxane (a) having vinyl groups at least at both terminals of a molecular chain is preferable.

The polysiloxane (a) is preferably linear and the polysiloxane (b) is preferably polysiloxane (b) in which —O—Si(CH$_3$)$_2$(CH=CH$_2$) is bonded to a Si atom constituting a main chain.

The polysiloxane (A) having a vinyl group and a phenyl group is subjected to hydrosilylation through a reaction with the polysiloxane (B) having two or more Si—H groups in the presence of a platinum catalyst. A cross-linked structure is formed through this hydrosilylation reaction (addition vulcanization reaction).

The content of the vinyl group of the polysiloxane (A) is not particularly limited. The content of the vinyl group is, for example, 0.01 to 5 mol % and preferably 0.05 to 2 mol % from the viewpoint of forming a sufficient network between components contained in a composition for an acoustic wave probe.

In addition, the content of the phenyl group of the polysiloxane (A) is not particularly limited. The content of the phenyl group is, for example, 1 to 80 mol % and preferably 2 to 40 mol % from the viewpoint of mechanical strength in a case where a silicone resin for an acoustic wave probe is made.

Here, the content of the vinyl group is mol % of a vinyl group-containing siloxane unit in a case where all units constituting the polysiloxane (A) are set to 100 mol %, In a case where all Si atoms of Si in a Si—O unit and at a terminal which constitute a main chain are substituted with at least one vinyl group, the content becomes 100 mol %.

Similarly, the content of the phenyl group is mol % of a phenyl group-containing siloxane unit in a case where all units constituting the polysiloxane (A) are set to 100 mol %. In a case where all Si atoms of Si in a Si—O unit and at a terminal which constitute a main chain are substituted with at least one phenyl group, the content becomes 100 mol %.

The "unit" of polysiloxane refers to Si atoms in a Si—O unit and at a terminal which constitute a main chain.

The degree of polymerization and the specific gravity are not particularly limited. The degree of polymerization is preferably 200 to 3000 and more preferably 400 to 2,000, and the specific gravity is preferably 0.9 to 1.1 from the viewpoint of improving the mechanical strength, the hardness, the chemical stability, and the like of an obtained silicone resin for an acoustic wave probe.

The mass average molecular weight of the polysiloxane (A) having a vinyl group and a phenyl group is preferably 10,000 to 200,000, more preferably 20,000 to 200,000, still more preferably 30,000 to 150,000, and particularly preferably 40,000 to 120,000 from the viewpoints of the mechanical strength, the hardness, and easiness of processing.

The mass average molecular weight can be measured using, for example, TOLUENE (manufactured by Shonan Wako Junyaku K.K.) as an eluent, TSKgel (registered trademark), G3000HXL+TSKgel (registered trademark), and G2000HXL as columns, and a RI detector under the conditions of a temperature of 23° C. and a flow rate of 1 mL/min after preparing a GPC apparatus HLC-8220 (manufactured by TOSOH CORPORATION).

The kinematic viscosity at 25° C. is preferably $1 \times 10^{-5}$ to 10 m$^2$/s, more preferably $1 \times 10^{-4}$ to 1 m$^2$/s, and still more preferably $1 \times 10^{-3}$ to 0.5 m$^2$/s.

The kinematic viscosity can be measured and obtained at a temperature of 23° C. using Ubbelohde-type viscometer (for example, a trade name of SU manufactured by SIBATA SCIENTIFIC TECHNOLOGY LTD.) in compliance with JIS Z8803.

Polysiloxane represented by General Formula (A) is preferable as the polysiloxane (a) having vinyl groups at least at both terminals of a molecular chain.

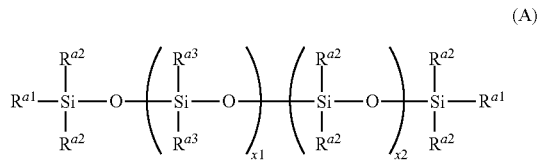

(A)

In General Formula (A), $R^{a1}$ represents a vinyl group and $R^{a2}$ and $R^{a3}$ each independently represent an alkyl group, a cycloalkyl group, an alkenyl group, or a phenyl group. x1 and x2 each independently represent an integer of 1 or more. Here, a plurality of $R^{a2}$'s and a plurality of $R^{a3}$'s may be the same as or different from each other, and at least one of the $R^{a2}$'s and $R^{a3}$'s represents a phenyl group. In addition, each of the groups of $R^{a2}$ and $R^{a3}$ may further be substituted with a substituent.

The number of carbon atoms in an alkyl group in $R^{a2}$ and $R^{a3}$ is preferably 1 to 10, more preferably 1 to 4, still more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group in $R^{a2}$ and $R^{a3}$ is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a2}$ and $R^{a3}$ is preferably 2 to 10, more preferably 2 to 4, and still more preferably 2. Examples of the alkenyl group include a vinyl group, an allyl group, and a butenyl group.

The alkyl group, the cycloalkyl group, the alkenyl group, and the phenyl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a2}$ and $R^{a3}$ are preferably an alkyl group, an alkenyl group, or a phenyl group, more preferably an alkyl group having 1 to 4 carbon atoms, a vinyl group, or a phenyl group, and still more preferably a methyl group, a vinyl group, or a phenyl group.

Among them, $R^{a2}$ is preferably a methyl group, and $R^{a3}$ is preferably a phenyl group. In addition, it is preferable that both $R^{a3}$'s in the repetition of x1 are phenyl groups.

x1 is preferably an integer of 1 to 3,000 and more preferably an integer of 5 to 1,000 x2 is preferably an integer of 1 to 3,000, and more preferably an integer of 40 to 1,000.

In the present invention, each of the repeating units "—Si($R^{a3}$)$_2$—O—" and "—Si($R^{a2}$)$_2$—O—" in General Formula (A) ma exist in a block-polymerized form or may be in a form in which the repeating units exist randomly.

Examples of the polysiloxane having vinyl groups at least at both terminals of a molecular chain include DMS series (for example DMS-V31, DMS-V31S15, DMS-V33, DMS-V35, DMS-V35R, DMS-V41, DMS-V42, DMS-V46, DMS-V51, and DMS-V52) which are trade names manufactured by GELEST, INC., and PDV series (for example, PDV-0341, PDV-0346, PDV-0535, PDV-0541, PDV-1631, PDV-1635, PDV-1641, and PDV-2335, PMV-9925, PVV-3522, FMV-4031, and EDV-2022) which are trade names manufactured by GELEST, INC., In the DMS-V31S15, Fumed silica is formulated into DMS-V31S15 in advance, and therefore, kneading using a special device is unnecessary.

The polysiloxane (A) having a vinyl group and a phenyl group in the present invention may be used singly or in combination of two or more thereof.

<The Polysiloxane (B) Having two or more Si—H Groups in Molecular Chain>

The polysiloxane (B) having two or more Si—H groups in a molecular chain used in the present invention (hereinafter, also simply referred to as polysiloxane (B) has two or more Si—H groups in a molecular chain. Here, in a case where the polysiloxane (B) has a "—SiH$_2$—" structure, the number of Si—H groups in the "—SiH$_2$—" structure is counted as two. In addition, in a case where the polysiloxane (B) has a "—SiH$_3$—" structure, the number of Si—H groups in the "—SiH$_3$—" structure is counted as three.

In a case where there are two or more Si—H groups in a molecular chain, it is possible to crosslink polysiloxane having at least two polymerizable unsaturated groups.

There is a linear structure and a branched structure in the polysiloxane (B), and the linear structure is preferable.

The mass average molecular weight of a linear structure is preferably 500 to 100,000 and more preferably 1,500 to 50,000 from the viewpoints of the mechanical strength and the hardness.

In addition, the polysiloxane (B) preferably has a phenyl group, and the content of the phenyl group is not particularly limited. The content of the phenyl group is, for example, 20 to 80 mol % and preferably 30 to 70 mol % from the viewpoint of mechanical strength in a case where a silicone resin for an acoustic wave probe is made.

Here, the content of the phenyl group is the content calculated by replacing the polysiloxane (A) with the polysiloxane (B) in the content of the phenyl group in the above-described polysiloxane (A).

The Si—H equivalent of the polysiloxane (B) is preferably less than or equal to 1,300 g/mol and more preferably less than or equal to 500 g/mol. In addition, the Si—H equivalent is preferably greater than or equal to 50 g/mol and more preferably greater than or equal to 100 g/mol.

In the present invention, it is preferable that both of the polysiloxane (A) and the polysiloxane (B) have a phenyl group since they improve compatibility.

In a case where the silicone resin for an acoustic wave probe of the present invention has a bulky phenyl group, it is possible to increase the acoustic velocity, the hardness, and the specific gravity. For this reason, it is possible to increase the acoustic impedance. As a result, it is possible to reduce the amount of zinc oxide to be added.

The polysiloxane (B) which has a linear structure and two or more Si—H groups in a molecular chain is preferably polysiloxane represented by General Formula (B).

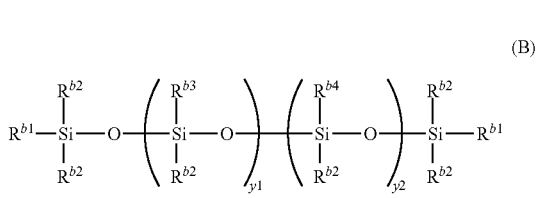
(B)

In General Formula (B), $R^{b1}$ and $R^{b2}$ each independently represent a hydrogen atom, an alkyl group, a cycloalkyl group, an aryl group, or $-O-Si(R^{b6})_2(R^{b5})$. $R^{b5}$ and $R^{b6}$ each independently represent a hydrogen atom, an alkyl group, a cycloalkyl group, or an aryl group. $R^{b3}$ and $R^{b4}$ each independently represent a hydrogen atom, an alkyl group, a cycloalkyl group, an alkenyl group, an aryl group, or $-O-Si(R^{b8})_2(R^{b7})$. $R^{b7}$ and $R^{b8}$ each independently represent a hydrogen atom, an alkyl group, a cycloalkyl group, an alkenyl group, or an aryl group. y1 represents an integer of 0 or more and y2 represents an integer of 1 or more. Here, a plurality of $R^{b1}$'s, a plurality of $R^{b2}$'s a plurality of $R^{b3}$'s, a plurality of $R^{b4}$'s, a plurality of $R^{b5}$'s, a plurality of $R^{b6}$'s, a plurality of $R^{b7}$'s, and a plurality of $Rb^{b8}$'s each may be the same as or different from each other. In addition, each of the groups of $R^{b1}$ to $R^{b8}$ may further be substituted with a substituent. However, there are two or more Si—H groups in a molecular chain.

An alkyl group and a cycloalkyl group in $R^{b1}$ and $R^{b2}$ are synonymous with an alkyl group and a cycloalkyl group in $R^{a2}$ and $R^{a3}$, and preferred ranges thereof are also the same as each other. An alkyl group, a cycloalkyl group, and an alkenyl group in $R^{b3}$ and $R^{b4}$ are synonymous with an alkyl group, a cycloalkyl group, and an alkenyl group in $R^{a2}$ and $R^{a3}$, and preferred ranges thereof are also the same as each other. The number of carbon atoms of an aryl group in to $R^{b1}$ and $R^{b4}$ is preferably 6 to 12, and more preferably 6 to 10, and still more preferably 6 to 8. Examples of the aryl group include a phenyl group, a tolyl group, and a naphthyl group.

An alkyl group, a cycloalkyl group, and an aryl group in $R^{b5}$ and $R^{b6}$ of $-O-Si(R^{b6})_2(R^{b5})$ are synonymous within alkyl group, a cycloalkyl group, and an aryl group in $R^{b1}$ and $R^{b2}$, and preferred ranges thereof are also the same as each other.

An alkyl group, a cycloalkyl group, and alkenyl group, and an aryl group in $R^{b7}$ and $R^{b8}$ of $-O-Si(R^{b8})_2(R^{b7})$ are synonymous with an alkyl group, a cycloalkyl group, an alkenyl group, and an aryl group in $R^{b3}$ and $R^{b4}$, an preferred ranges thereof are also the same as each other.

$R^{b1}$ and $R^{b2}$ are preferably a hydrogen atom, an alkyl group, an aryl group, or $-O-Si(R^{b6})_2(R^{b5})$, and more preferably a hydrogen atom, an alkyl group have 1 to 4 carbon atoms, a phenyl group, or $-O-Si(CH_3)_2H$.

$R^{b3}$ and $R^{b4}$ are preferably a hydrogen atom, an alkyl group, an alkenyl group, an aryl group, or $-O-Si(R^{b8})_2(R^{b7})$, and more preferably a hydrogen atom, an alkyl group have 1 to 4 carbon atoms, a vinyl group, a phenyl group, or $-O-Si(CH_3)_2H$.

Among them, $R^{b1}$ and $R^{b2}$ are preferably a hydrogen atom, an alkyl group, or an aryl group, more preferably a hydrogen atom or an alkyl group, and still more preferably a hydrogen atom or a methyl group. In addition, a combination of $R^{b1}$ as a hydrogen atom and $R^{b2}$ as a methyl group is preferable.

$R^{b3}$ is preferably a hydrogen atom, an alkyl group, an alkenyl group, an aryl group, or $-O-Si(R^{b8})_2(R^{b7})$, more preferably a hydrogen atom or an alkyl group, and particularly preferably a hydrogen atom.

$R^{b4}$ is preferably a hydrogen atom an alkyl group, an alkenyl group, an aryl group, or $-O-Si(R^{b8})_2(R^{b7})$, more preferably a hydrogen atom, an alkyl group, or an aryl group, still more preferably a hydrogen atom, a methyl group, or a phenyl group, still more preferably a methyl group or a phenyl group, and particularly preferably a phenyl group.

y1 is preferably an integer of 1 or more.

y1+y2 is preferably an integer of 5 to 2,000, more preferably an integer of 7 to 1,000, still more preferably an integer of 10 to 50, and particularly preferably an integer of 15 to 30.

Each of "$-Si(R^{b3})_2-O-$" and "$-Si(R^{b4})_2-O-$" in General Formula (B) in the present invention may exist in a block-polymerized form in polysiloxane or may be in a form in which they exist randomly in polysiloxane.

As a combination of $R^{b1}$ to $R^{b3}$, a combination of a hydrogen atom or an alkyl group having 1 to 4 carbon atoms as an alkyl group having 1 to 4 carbon atoms as $R^{b2}$, and a hydrogen atom as $R^{b3}$ is preferable and a combination of an alkyl group having 1 to 4 carbon atoms as $R^{b1}$, an alkyl group having 1 to 4 carbon atoms as $R^{b2}$, and a hydrogen atom as $R^{b3}$ is more preferable.

Examples of the polysiloxane (B) with a linear structure include HMS-151 (Si—H equivalent of 490 g/mol). HMS-301 (Si—H equivalent of 245 g/mol), HMS-501 (Si—H equivalent of 135 g/mol), and HMS-064 (Si—H equivalent of 1,240 g/mol) which are methylhydrosiloxane-dimethylsiloxane copolymers (trimethylsiloxy terminated), HMS-991 (Si—H equivalent of 67 g/mol) which is a methylhydrosiloxane polymer (trimethylsiloxy terminated), and HPM-502 (Si—H equivalent of 165 g/mol) which is a methylhydrosiloxane-phenylmethylsiloxane copolymer (hydride terminated) (all are trade names of GELEST, INC.).

It is preferable that both the linear structure and the branched structure have no vinyl group from the viewpoint of preventing the progress of a crosslinking reaction within a molecule. Among these, it is preferable that the branched structure has no vinyl group.

The polysiloxane (B) which has a branched structure and two or more Si—H groups in a molecular chain has a branched structure and two or more hydrosilyl groups (Si—H groups).

The specific gravity is preferably 0.9 to 0.95.

The polysiloxane (B) with a branched structure is preferably represented by Average Composition Formula (b).

Average Composition Formula (b): $[H_a(R^{b9})_{3a}SiO_{1/2}]_{y3}[SiO_{4/2}]_{y4}$ Here, $R^{b9}$ represents an alkyl group, a cycloalkyl group, an alkenyl group, or an aryl group, a represents 0.1 to 3, and y3 and y4 each independently represent an integer of 1 or more.

An alkyl group, a cycloalkyl group, an alkenyl group, and an aryl group in $R^{b9}$ are synonymous with an alkyl group, a cycloalkyl group, an alkenyl group, and an aryl group in $R^{b3}$ and $R^{b4}$, and preferred ranges thereof are also the same as each other.

a is preferably 1.

The content ratio of a hydrosilyl group represented by a/3 is preferably greater than 0.1 and less than 0.6 and more preferably greater than 0.1 and less than 0.4.

In contrast, in a case of representing the polysiloxane (B) with a branched structure using a chemical structural formula, polysiloxane in which $-O-Si(CH_3)_2(H)$ is bonded to a Si atom constituting a main chain is preferable and polysiloxane having a structure represented by General Formula (Bb) is more preferable.

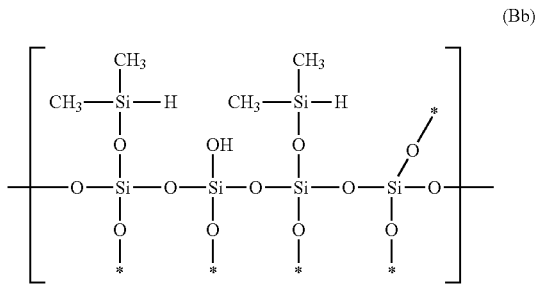

(Bb)

In General Formula (Bb), * means a bond with at least a Si atom of siloxane.

Examples of the polysiloxane (B) with a branched structure include HQM-107 (trade name of Hydride Q Resin manufactured by GELEST, INC.) and HDP-111 (trade name of polyphenyl-(dimethylhydroxy)siloxane (hydride terminated), [(HM$_{e2}$SiO)(C$_6$H$_5$Si)O]: 99 to 100 mol % manufactured by GELEST, INC.).

Me is CH$_3$.

The polysiloxane (B) having two or more Si—H groups in a molecular chain in the present invention may be used singly, or in combination of two or more thereof/ In addition, the polysiloxane (B) with a linear structure and the polysiloxane (B) with a branched structure may be used in combination.

<Zinc Oxide>

In the present invention, zinc oxide is added in order to increase the acoustic impedance and reduce the acoustic attenuation factor. The average primary particle diameter of zinc oxide used in the present invention is preferably 10 nm to 200 nm, more preferably 15 nm to 100 nm, and particularly preferably greater than or equal to 20 nm and less than 50 nm.

In a case where the average primary particle diameter of zinc oxide used in the present invention is within the above-described ranges, it is considered that zinc oxide particles function s stoppers in a case where mechanical stress is applied to the silicone resin for an acoustic wave probe. Particularly, the distance between particles becomes shorter in a case where the average primary particle diameter is small. Therefore, it is considered that the functions as stoppers are more favorably exhibited.

As a result, it is considered that the acoustic impedance is increased, the increase in acoustic attenuation is suppressed, and the hardness and the mechanical strength (tear strength and abrasion resistance) of the silicone resin for an acoustic wave probe are improved.

The average primary particle diameter is disclosed in the catalog of the manufacturer of zinc oxide. However, for zinc oxide of which the average primary particle diameter has not been disclosed in the catalog, or for zinc oxide newly manufactured, it is possible to obtain the average primary particle diameter by averaging the particle diameters measured using a transmission electron microscope (transmission electron microscopy: TEM). That is, the minor axis and the major axis of a particle of an electron micrograph photographed through TEM were measured and an average value thereof was obtained as the particle diameter of a particle. In the present invention, the particle diameters 300 or more particles which have been randomly selected are averaged and the averaged particle diameter is obtained as the average primary particle diameter.

In addition, in a case where surface treatment to be described below is performed on zinc oxide, the average primary particle diameter means an average primary particle diameter in a state in which the surface treatment has been performed.

Commercially available zinc oxide can be used, and examples thereof include FINEX-30S-LPT, FINEX-50S-LPT, FINEX-30, FINEX-30W-LP2, and FINEX-25-LPT all are trade names) manufactured by SAKAI CHEMICAL INDUSTRY CO., LTD.

Zinc oxide may be used singly or in combination of two or more thereof.

Zinc oxide particles of which the surfaces have been treated are preferable and zinc oxide particles which have been subjected to surface treatment using a silane compound are more preferable as zinc oxide used in the present invention.

By treating the surfaces of zinc oxide particles using a silane compound, interaction with the silicone resin becomes stronger and affinity to the silicone resin becomes higher. Therefore, it is considered that it is possible to finely disperse zinc oxide particles with a small average primary particle diameter. For this reason, the zinc oxide particles more favorably exhibit functions as stoppers in a case where mechanical stress is applied, and therefore, it is considered that the hardness and the mechanical strength of the silicone resin are improved.

A usual technique may be used as a technique of the surface treatment. Examples of the technique of the surface treatment using a silane compound include a technique of performing surface treatment using a silane coupling agent and a technique of performing coating using a silicone compound. In the present invention, the technique of performing coating using a silicone compound is preferable.

(i) Silane Coupling Agent

A silane coupling agent having a hydrolyzable group is preferable as a silane coupling agent from the viewpoint of improving the hardness and the mechanical strength of a silicone resin. Surface modification of zinc oxide particles is performed such that a hydrolyzable group in a silane coupling agent becomes a hydroxyl group after being hydrolyzed using water and this hydroxyl group is subjected to a dehydration and condensation reaction with a hydroxyl group or the surfaces of the zinc oxide particles, thereby improving the hardness and the mechanical strength of an obtained silicone resin. Examples of the hydrolyzable group include an alkoxy group, an acyloxy group, and a halogen atom.

In a case where the surfaces of zinc oxide particles are hydrophobically modified, affinity between the zinc oxide particles, the polysiloxane (A) and the polysiloxane (B) becomes favorable, and therefore, the hardness and the mechanical strength of an obtained silicone resin are improved, which is preferable.

Examples of a silane coupling agent having a hydrophobic group as a functional group include alkoxysilanes such as methyltrimethoxysilane, dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, and decyltrimethoxysilane: chlorosilanes such as methyltrichlorosilane, dimethyldichlorosilane (DDS), trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane. methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilane such as vinyltrichlorosilane and vinylmethyldichlorosilane; and divinyltetramethyldisilazane.

Zinc oxide particles treated using a trialkylsilylating agent are preferable and zinc oxide particles treated using a trimethylsilylating agent are more preferable as the zinc oxide particles subjected to surface treatment using a silane coupling agent.

Examples of the same compound include the above-described silane coupling agents and a silane coupling agent in which a functional group in a silane coupling agent is substituted with an alkyl group.

In addition, examples of the trimethylsilylating agent include trimethylchlorosilane and hexamethyldisilazane (HMDS) described in the above-described silane coupling agent, sod trimethylmethoxysilane which is a silane coupling agent in which a functional group is substituted with an alkyl group.

Examples of a commercially available silane coupling agent include hexamethyldisilazane (HMDS) (trade name: HEXAMETHYLDISILAZANE (SIH6110.1), manufactured by GELEST, INC.).

A hydroxyl group existing on the surfaces of zinc oxide particles is covered with a trimethylsilyl group through a reaction with hexamethyldisilazane (HMDS) and the surfaces of the zinc oxide particles are hydrophobically modified.

(ii) Silicone Compound

A silicone compound with which the zinc oxide particles are coated may be a polymer formed through siloxane bonding.

Examples of the silicone compound include a silicone compound in which all or a part of side chains and/or terminals of polysiloxane has become a methyl group, a silicone compound in which a part of a side chain is a hydrogen atom, a modified silicone compound in which organic groups such as an amino group or an epoxy group is introduced into all or a part of side chains and/or terminals, and a silicone resin having a branched structure. The silicone compound may be either of a linear structure or a cyclic structure.

Examples of the silicone compound in which all or a part of side chains and/or terminals of polysiloxane has become a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated): and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethyisiloxane copolymer (hydride terminated), polymethylhydrosiloxane (hydride terminated), polymethylhydrosiloxane (trimethylsiloxy-terminated), polyethylhydrosiloxane (triethylsiloxy terminated), polyphenyl-(dimethylhydrosiloxy) siloxane (hydride terminated), and methylhydrosiloxane-phenylmethylsiloxane copolymer (hydride terminated), and methylhydrosiloxane-octylmethylsiloxane copolymer-terpolymer.

In addition, examples of modified silicone into which an organic group is introduced include reactive silicone into which an amino group, an epoxy group, a methoxy group, a (meth)acryloyl group, a phenol group, a carboxylic anhydride group, a hydroxy group, a mercapto group, a carboxyl group, and an organic group of a hydrogen atom are introduced; and non-reactive silicone modified with polyether, aralkyl, fluoroalkyl, long chain alkyl, long chain aralkyl, higher fatty acid ester, higher fatty acid amide, and polyether methoxy.

Zinc oxide particles coated with a silicone compound can be obtained through a usual method. For example, the zinc oxide particles can be obtained by being mixed and stirred in dimethylpolysiloxane for a certain period of time and being filtered.

In addition, in a case of using reactive modified silicone as a silicone compound, surface modification of zinc oxide particles is performed through reaction of an organic group with a hydroxyl group of the surfaces of the zinc oxide particles, and therefore, the hardness or the mechanical strength of an obtained silicone resin is improved.

An Example of the commercially available silicone compound includes methyl hydrogen silicone oil (MHS) (trade name: KF-99, manufactured by Shin-Etsu Chemical Co., Ltd.) which is polymethylhydrosiloxane (trimethylsiloxy terminated).

In general, the vinyl group possessed by the polysiloxane (A) and the Si—H group possessed by the polysiloxane (B) stoichiometrically react with each other in a ratio of 1:1.

However, in the present invention, the space between the polysiloxane (A) and the polysiloxane (B) is densely filled with the zinc oxide particles. Therefore, the movement of molecular chains of the polysiloxane (A) and the polysiloxane (B) is restricted.

Accordingly, the equivalent of the Si—H group possessed by the polysiloxane (B) to the vinyl group possessed by the polysiloxane (A) for a reaction between all the vinyl groups with the Si—H groups is preferably vinyl group: Si—H group=1:1.1 to 1:8 and more preferably 1:1.2 to 1:5.

<Other Components>

In the composition for an acoustic wave probe of the present invention, it is possible to appropriately formulate a platinum catalyst for an addition polymerization reaction, a vulcanization retardant, a solvent, a dispersant, a pigment, a dye, an antistatic agent, an antioxidant, a flame retardant, a thermal conductivity enhancer in addition to the polysiloxane (A) having a vinyl group and a phenyl group, the polysiloxane (B) having two or more Si—H groups in a molecular chain, and zinc oxide.

<Catalyst>

Examples of the catalyst include platinum or a platinum-containing compound (hereinafter, also referred to as a "platinum compound"). Any platinum or platinum compound can be used.

Specific examples thereof include platinum black: a catalyst in which platinum is carried on an inorganic compound, carbon black, or the like: platinum chloride or an alcohol solution of platinum chloride; a complex salt of platinum chloride and olefin; and a complex salt of platinum chloride and vinyl siloxane. The catalyst may be used singly, or two or more thereof may be used in combination.

The content of a catalyst can appropriately be set within a range of the amount of catalyst.

The catalyst is necessary in the hydrosilylation reaction in which the Si—H group of the polysiloxane (B) is added to the vinyl group of the polysiloxane (A). The polysiloxane (A) is cross-linked by the polysiloxane (B) through an addition vulcanization reaction due to hydrosilylation to form a silicone resin.

Here, the catalyst may be contained in the composition for an acoustic wave probe of the present invention or may be brought into contact with the composition for an acoustic wave probe without being contained in the composition for an acoustic wave probe. The latter ease is preferable.

An example of a commercially available platinum catalyst includes a platinum compound (trade name: PLATINUM CYCLOVINYLMETHYLSILOXANE COMPLEX IN CYCLIC METHYLVINYLSILOXANES (SIP6832.2).

In a case where there is a catalyst in a polysiloxane mixture, the content of the catalyst present with respect to 100 parts by mass of the polysiloxane mixture is, as a Pt amount, preferably greater than or equal to 0.00001 parts by mass, move preferably greater than or equal to 0.00002 parts by mass, still more preferably greater than or equal to 0.00005 parts by mass, and particularly preferably greater than or equal to 0.0001 parts by mass from the viewpoint of reactivity. On the other hand, less than or equal to 0.1 parts by mass is preferable, less than or equal to 0.05 parts by mass is more preferable, less than or equal to 0.0.1 parts by mass is still more preferable, and less than or equal to 0.005 parts by mass is particularly preferable.

In addition, it is possible to control the vulcanization temperature by selecting an appropriate platinum catalyst. For example, platinum-vinyldisiloxane is used for room temperature vulcanization (RTV) at lower than or equal to 50° C. and platinum-cyclic vinysiloxane is used for high temperature vulcanization (HTV) at higher than or equal to 130° C.

<Method for Producing Composition for Acoustic Wave Probe and Silicone Resin for Acoustic Wave Probe>

The composition for an acoustic wave probe of the present invention can be prepared through a usual method.

For example, the composition for an acoustic wave probe can be obtained by kneading components constituting the composition for an acoustic wave probe using a kneader, a pressure kneader, a Banbury mixer (continuous kneader), and a kneading device with two rolls. The order of mixing the components is not particularly limited.

It is preferable to first make a polysiloxane mixture in which zinc oxide particles are dispersed in the polysiloxane (A) having a vinyl group and phenyl group and the polysiloxane (B) having two or more Si—H groups in a molecular chain, from the viewpoint of obtaining a homogeneous composition. Thereafter, it is possible to prepare a composition for an acoustic wave probe after adding a catalyst to the polysiloxane mixture, in which zinc oxide particles are dispersed, and performing defoamation under reduced pressure.

It is possible to obtain a silicone resin for an acoustic wave probe of the present invention by vulcanizing the composition for an acoustic wave probe of the present invention which has been obtained in this manner. Specifically, it is possible to obtain a silicone resin for an acoustic wave probe by, for example, thermally vulcanizing the composition for an acoustic wave probe for 5 minutes to 500 minutes at 20° C. to 200° C.

<Mechanical Strength and Acoustic Characteristics of Silicone Resin>

Hereinafter, the mechanical strength and acoustic characteristics of a silicone resin will be described in detail.

Here, ultrasonic characteristics among acoustic characteristics will be described. However, the acoustic characteristics are not limited to ultrasonic characteristics, and relates to acoustic characteristics at an appropriate frequency which is selected in accordance with a test object, measurement conditions, or the like.

[Hardness]

The hardness is preferably greater than or equal to 25 and more preferably greater than or equal to 30. A practical upper limit value is less than or equal to 80. In a case where the hardness is within the above-described ranges, it is possible to prevent deformation in a case of using a resin in an embedded form as a part of an acoustic wave probe.

The hardness of a silicone resin sheet can be obtained through a measurement method described in the section of examples described below.

[Tear Strength Test]

The tear strength is preferably greater than or equal to 6 N/cm, and more preferably greater than or equal to 10 N/cm. A practical upper limit value is less than or equal to 100 N/cm.

The tear strength can be obtained through the measurement method described in the section of examples to be described below.

[Taber Abrasion Test]

A Taber abrasion test is performed on a silicone resin sheet with a thickness of 2 mm in accordance with JIS K6264-2 (2005) to evaluate abrasion resistance.

The decrease in mass before and after the test is, from the viewpoint of suppressing the abrasion of a probe coming into contact with the human body, preferably less than or equal to 0.5%, more preferably less than or equal to 0.4%, and still more preferably less than or equal to 0.3%. A smaller value is preferable.

[Acoustic Impedance]

Acoustic impedance of a silicone resin sheet closer to acoustic impedance ($1.4 \times 10^6$ to $1.7 \times 10^6$ kg/m$^2$/sec) of a living body is preferable. The acoustic impedance of the silicone resin sheet of the present invention is preferably 1.2 to 1.8 kg/m$^2$/sec, more preferably 1.3 to 1.7 kg/m$^2$/sec, and particularly preferably 1.4 to 1.6 kg/m$^2$/sec.

The acoustic impedance of a silicone resin can be obtained through the measurement method described in the section of examples described below.

[Acoustic (Ultrasonic) Sensitivity]

In an evaluation system in the present invention, the acoustic (ultrasonic) sensitivity is preferably greater than or equal to −74 dB and more preferably greater than or equal to −73 dB.

The acoustic (ultrasonic) sensitivity can be obtained through the measurement method described in the section of examples described below.

The composition for an acoustic wave probe of the present invention is useful for medical members and can preferably be used, for example, in an acoustic wave probe or an acoustic wave measurement apparatus. The acoustic wave measurement apparatus of the present invention is not limited to an ultrasound diagnostic apparatus or a photoacoustic wave measurement apparatus, and is referred to as an apparatus that receives an acoustic wave which has been reflected or generated from a test object and displays the received acoustic wave as an image or a signal strength.

Particularly, the composition for an acoustic wave probe of the present invention can suitably be used in: a material of an acoustic matching layer which is provided in an acoustic lens of an ultrasound diagnostic apparatus or between a piezoelectric element and the acoustic lens and plays a role of matching acoustic impedance between the piezoelectric element and the acoustic lens; a material of an acoustic lens in a photoacoustic wave measurement apparatus or an ultrasound endoscope; and a material or the like of an acoustic lens in an ultrasound probe including capacitive micromachined ultrasonic transducers (cMUT) as an ultrasonic transducer array.

Specifically, the silicone resin for an acoustic wave probe of the present invention is preferably applied to, for example, an ultrasound diagnostic apparatus disclosed in JP2005-253751A and JP2003-169802A or an acoustic wave measurement apparatus such as a photoacoustic wave measurement apparatus disclosed in JP2013-202050A, JP2013-188465A, JP2013-180330A, JP2013158435A, JP2013-154139A, or the like.

<Acoustic Wave Probe>

A configuration of an acoustic wave probe of the present invention will be described below in more detail based on a configuration of an ultrasound probe in an ultrasound diagnostic apparatus which is described in FIG. 1. The ultrasound probe is a probe which particularly uses an ultrasonic wave as an acoustic wave in an acoustic wave probe. For this reason, a basic configuration of the ultrasound probe can be applied to the acoustic wave probe as it is.

<Ultrasound Probe>

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coining into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO and AlN $Pb(Zr,Ti)O_3$-based sintered body, and the like are widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is disclosed in JP2011-071842A or the like.

In the present invention it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layers>

The acoustic matching layer 2 is provided in order to reduce the difference in acoustic impedance between the piezoelectric element layer 3 and a test object and to efficiently transmit and receive an ultrasonic wave.

A composition for an ultrasound probe of the present invention can preferably be used as a material for the acoustic matching layer since the difference in acoustic impedance ($1.4 \times 10^6$ to $1.7 \times 10^6$ kg/m²/sec) between the piezoelectric element layer and the human body is small. The acoustic matching layer of the present invention preferably contains 10 mass % or more of a silicone resin for an acoustic wave probe obtained by subjecting the composition for an acoustic wave probe of the present invention to a vulcanization reaction.

<Acoustic Lens>

The acoustic lens 1 is provided in order to improve resolution by making an ultrasonic wave converge in a slice direction using refraction. In addition, it is necessary for the acoustic lens to achieve matching of an ultrasonic wave with acoustic impedance ($1.4 \times 10^6$ to $1.7 \times 10^6$ kg/m²/sec in a case of a human body) of a living body which is a test object after being closely attached to the living body and to reduce ultrasonic attenuation of the acoustic lens 1 itself.

That is, sensitivity of transmission and reception of an ultrasonic wave is improved in a case where the material of the acoustic lens 1 of which the acoustic velocity is sufficiently lower than that of the human body, the ultrasonic attenuation is low, and the acoustic impedance is close to a value of the skin of a living body such as the human body, as the material of the acoustic lens 1.

The composition for an ultrasound probe of the present invention can also preferably be used as a material of the acoustic lens. The acoustic lens of the present invention preferably contains greater than or equal to 10 mass % of the silicone resin for an acoustic wave probe obtained by subjecting the composition for an acoustic wave probe of the present invention to a vulcanization reaction.

The operation of the ultrasound probe 10 having such a configuration will be described. The piezoelectric element layer 3 is resonated alter applying voltage to the electrodes provided on both sides of a piezoelectric element, and an ultrasonic signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the composition for ultrasound probe of the present invention as a general medical ultrasonic transducer. Particularly a remarkable effect of improving the sensitivity can particularly be expected from a transmission frequency of an ultrasonic wave of greater than or equal to 10 MHz.

Hereinafter, an apparatus in which the acoustic lens obtained from the composition for an ultrasound probe of the present invention exhibits a function particularly regarding conventional problems will be described in detail.

The composition for an ultrasound probe of the present invention exhibits an excellent effect even with respect to other apparatuses disclosed below.

<Ultrasound Probe Including Capacitive Micromachined Ultrasonic Transducer (cMUT)>

In a case where cMUT apparatuses disclosed in JP2006-157320A, JP2011-71842A, and the like are used in an ultrasonic diagnostic transducer array, the sensitivity thereof generally becomes low compared to a transducer in which usual piezoelectric ceramics (PZT) is used.

However, it is possible to make up for deficient sensitivity of cMUT using the acoustic lens obtained from the composition for an acoustic wave probe of the present invention. Accordingly, it is possible to make the sensitivity of cMUT to performance of a conventional transducer.

The cMUT apparatus is manufactured, through MEMS technology. Therefore, it is possible to provide an inexpensive ultrasound probe, of which mass productivity is higher than that of a piezoelectric ceramics probe, to the market.

<Photoacoustic Wave Measurement Apparatus Using Photoultrasonic Imaging>

Photoultrasonic imaging (photo acoustic imaging: PAI) disclosed in JP2013-158435A or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the composition for an acoustic wave probe of the present invention.

<Ultrasound Endoscope 22

In an ultrasonic wave in an ultrasound endoscope disclosed in JP2008-311700A or the like, a signal line cable is structurally long compared to that of a transducer for a body surface, and therefore, there is a problem of improving the sensitivity of the transducer caused by loss of the cable. Regarding this problem, it is said that there are no effective means for improving the sensitivity due to the following reasons.

First, in a case of an ultrasound diagnostic apparatus for a body surface, it is possible to install an amplifier circuit, an AD conversion IC, or the like at a distal end of the transducer. In contrast the ultrasound endoscope is inserted into a body. Therefore, there is no installation space within the transducer, and thus, it is difficult to install the amplifier circuit, the AD conversion IC, or the like at a distal end of the transducer.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is generally a probe having an ultrasonic transmission frequency of greater than or equal to 7 to 8 MHz, and therefore, it is also difficult to improve the sensitivity due to piezoelectric single crystal material.

However, it is possible to improve the sensitivity of the ultrasonic transducer for an endoscope using the acoustic lens obtained from the composition for an acoustic wave probe of the present invention.

In addition, even in a case of using the same ultrasonic transmission frequency (for example, 10 MHz), the efficacy is particularly exhibited in a case of using the acoustic lens obtained from the composition for an acoustic wave probe of the present invention in the ultrasonic transducer for an endoscope.

EXAMPLES

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like.

In the following examples, unless otherwise specified, "parts" and "%" are on a mass basis. In addition, "to" used in Table means that the composition is not included.

Example 1

55.3 parts by mass of a vinyl terminated diphenylsiloxane-dimethylsiloxane copolymer (component (A) in Table 1, manufactured by GELEST, INC., trade name of "PDV-0541", mass average molecular weight of 60,000, amount of diphenylsiloxane 5 mol %) as polysiloxane (A), 0.7 parts by mass of methylhydrosiloxane polymer (component (B) in Table 1, manufactured by GELEST, INC., trade name of "HMS-991", mass average molecular weight of 1,600, Si—H equivalent of 67 g/mol) as polysiloxane (B), and 44.0 parts by mass of zinc oxide ("FINEX (registered trademark)-50S-LPT manufactured by SAKAI CHEMICAL INDUSTRY CO., LTD., average primary particle diameter of 20 nm, silicone surface treatment) were kneaded using a kneader for 2 hours at a temperature of 23° C. to make a homogeneous paste (polysiloxane mixture). 500 ppm of a platinum catalyst solution (manufactured by GELEST, INC., trade name of "SIP6832.3" with 2 mass % of Pt concentration) was added to and mixed with the paste. Then, the mixture was subjected to defoamation under reduced pressure (1 mmHg), was placed in a metal mold of 150 mm long×150 mm wide×2 mm depth, and was subjected to heat treatment for 3 hours at 60° C. to produce a silicone resin for an acoustic wave probe (sheet of 150 mm long×150 mm wide×2 mm thick). Hereinafter, the silicone resin for an acoustic wave probe produced in this manner is referred to as a "silicone resin sheet".

In Table 1, the "polysiloxane mixture" is simply described as a "mixture".

Examples 2 to 22 and Comparative Examples 1 to 5

Predetermined silicone resin sheets were obtained similarly to Example 1 except that the composition of the polysiloxane mixture of Example 1 was changed to the compositions disclosed in Table 1.

Here, Comparative Examples 2 and 3 are supplementary tests in which examples in JP2005-125071A is imitated.

<Evaluation of Mechanical Strength and Ultrasonic Characteristics>

The following evaluation was performed on silicone resin sheets of Example 1 to 22 and Comparative Examples 1 to 5.

[Hardness]

The type A durometer hardness of each of the obtained silicone resin sheets with a thickness of 2 mm was measured using a rubber hardness meter (trade name "RH-201A" manufactured by Excel co., Ltd.) in compliance with JIS K6253-3 (2012).

[Tear Strength Test]

A trouser-type test piece of a silicone resin sheet with a thickness of 2 mm was manufactured and the tear strength was measured in compliance with JIS K6252 (2007).

[Taber Abrasion Test]

The obtained silicone resin sheets with a thickness of 2 mm were rotated 1,000 times under the conditions of an abrasion wheel of CS-10, a load of 4.9 N, and a rotation speed of 60 rpm using a Taber abrasion tester manufactured by Toyo Seiki Seisaku-sho, Ltd. in accordance with JIS K6264-2 (2005). Each mass before and after the test was measured, and the decrease in mass (%) before and after the test was calculated from the following expression. In Table 1, the decrease in mass was described as the Taber abrasion amount [%].

(Mass of Silicone Resin Sheet Before Test—Mass of Silicone Resin Sheet after Test)×100

[Acoustic Impedance]

The density of each of the obtained silicone resin sheets with a thickness of 2 mm at 25° C. was measured using an electronic gravimeter ("SD-200L" manufactured by ALFA MIRAGE) in accordance with a density measurement method of an method A (underwater substitution method) disclosed in JIS K711.2 (1999). The acoustic velocity of an ultrasonic wave was measured at 25° C. using a sing-around type acoustic velocity measurement apparatus ("UVM-2 type" manufactured by Ultrasonic Engineering Co., LTd.) in compliance with JIS Z2353 (2003) and acoustic impedance was obtained from a sum of the density and the acoustic velocity which had been measured.

[Acoustic (Ultrasonic) Sensitivity]

A sinusoidal signal (a wave) of 5 MHz which had been output from an ultrasonic oscillator (a function generator with a trade name of "FG-350" manufactured by IWATSU ELECTRIC CO., LTD.) was input into an ultrasound probe (manufactured by JAPAN PROBE), and an ultrasonic pulse wave with a center frequency of 5 MHz was generated in water from the ultrasound probe. The magnitude of the amplitude before and after the generated ultrasonic wave passed through each of the obtained silicone resin sheet with a thickness of 2 mm was measured in a water temperature environment of 25° C. using an ultrasonic receiver (an oscilloscope with a trade name of "VP-5204A" manufactured by Matsushita Electric Industrial Co., LTd.). The acoustic (ultrasonic) attenuation of each material was compared with each other by comparing the acoustic (ultrasonic) sensitivities of each material.

The acoustic (ultrasonic) sensitivity was calculated using the following calculation equation by setting a voltage value obtained in a case where the acoustic (ultrasonic) wave generated with respect to a voltage peak value Vin of a wave with a half-width of less than or equal to 50 nsec which had been input using the ultrasonic oscillator passed through the sheet and the ultrasonic oscillator received the acoustic (ultrasonic) wave which had been reflected from a surface facing the sheet, as Vs.

Acoustic (Ultrasonic) Sensitivity=20×Log (Vs/Vin)

The obtained results were summarized and shown in Table 1.

In table 1. the mass average molecular weight of the polysiloxane (A) and the polysiloxane (B) is simply described as a molecular weight, and the type of each component is indicated by a trade name. In addition, the Si—H equivalent is simply described as equivalent.

TABLE 1

| | | | | Example 1 | Example 2 | Example 3 | Example 4 | Example 5 | Example 6 | Example 7 |
|---|---|---|---|---|---|---|---|---|---|---|
| Mixture composition | Polysiloxane | Component (A) | Type | PDV-0541 | PDV-0535 | PDV-1641 | PDV-1635 | PDV-1631 | PDV-0541 | PDV-0541 |
| | | | Molecular weight | 60,000 | 47,500 | 55,000 | 35,300 | 19,000 | 60,000 | 60,000 |
| | | | Content [parts by mass] | 55.3 | 55.2 | 69.9 | 68.8 | 66.4 | 51.8 | 53.8 |
| | | Component (B) | Type | HMS-991 | HMS-991 | HPM-502 | HPM-502 | HPM-502 | HMS-151 | HMS-301 |
| | | | Molecular weight | 1,600 | 1,600 | 4,500 | 4,500 | 4,500 | 2,000 | 2,000 |
| | | | Equivalent [g/mol] | 67 | 67 | 165 | 165 | 165 | 490 | 245 |
| | | | Content [parts by mass] | 0.7 | 0.8 | 2.1 | 3.2 | 5.6 | 4.2 | 2.2 |
| | Zinc oxide | | Type | 50S-LPT | 50S-LPT | 50S-LPT | 50S-LPT | 50S-LPT | 50S-LPT | 50S-LPT |
| | | | Average primary particle diameter [nm] | 20 | 20 | 20 | 20 | 20 | 20 | 20 |
| | | | Content [mass %] | 44.0 | 44.0 | 28.0 | 28.0 | 28.0 | 44.0 | 44.0 |
| Evaluation | | | JIS hardness | 41 | 43 | 39 | 41 | 43 | 31 | 34 |
| | | | Tear strength [N/cm] | 13 | 11 | 10 | 8 | 6 | 11 | 15 |
| | | | Taber abrasion amount [%] | 0.14 | 0.17 | 0.09 | 0.11 | 0.13 | 0.33 | 0.25 |
| | | | Acoustic impedance [×10$^4$ kg/m$^2$/sec] | 1.41 | 1.41 | 1.54 | 1.54 | 1.53 | 1.40 | 1.40 |
| | | | Acoustic (ultrasonic) sensitivity [dB] | −72.4 | −72.1 | −71.3 | −71.1 | −70.9 | −71.7 | −72.0 |

| | | | | Example 8 | Example 9 | Example 10 | Example 11 | Example 12 | Example 13 | Example 14 |
|---|---|---|---|---|---|---|---|---|---|---|
| Mixture composition | Polysiloxane | Component (A) | Type | PDV-0541 | PDV-0541 | PDV-0541 | PDV-0541 | PDV-0541 | PDV-0541 | PDV-0541 |
| | | | Molecular weight | 60,000 | 60,000 | 60,000 | 60,000 | 60,000 | 60,000 | 60,000 |
| | | | Content [parts by mass] | 54.7 | 46.4 | 55.3 | 55.3 | 55.3 | 55.3 | 55.3 |
| | | Component (B) | Type | HMS-501 | HMS-064 | HMS-991 | HMS-991 | HMS-991 | HMS-991 | HMS-991 |
| | | | Molecular weight | 1,100 | 60,000 | 1,600 | 1,600 | 1,600 | 1,600 | 1,600 |
| | | | Equivalent [g/mol] | 135 | 1,240 | 67 | 67 | 67 | 67 | 67 |
| | | | Content [parts by mass] | 1.3 | 9.6 | 0.7 | 0.7 | 0.7 | 0.7 | 0.7 |
| | Zinc oxide | | Type | 50S-LPT | 50S-LPT | 75 | 50S-LP2 | 50 | 30S-LPT | 30W-LP2 |
| | | | Average primary particle diameter [nm] | 20 | 20 | 15 | 20 | 20 | 35 | 35 |
| | | | Content [mass %] | 44.0 | 44.0 | 44.0 | 44.0 | 44.0 | 44.0 | 44.0 |

TABLE 1-continued

| Evaluation | | | | JIS hardness | 37 | 28 | 44 | 42 | 43 | 41 | 43 |
|---|---|---|---|---|---|---|---|---|---|---|---|
| | | | | Tear strength [N/cm] | 14 | 16 | 22 | 14 | 17 | 12 | 11 |
| | | | | Taber abrasion amount [%] | 0.17 | 0.37 | 0.33 | 0.19 | 0.31 | 0.10 | 0.08 |
| | | | | Acoustic impedance [×10$^4$ kg/m$^2$/sec] | 1.41 | 1.37 | 1.42 | 1.41 | 1.42 | 1.41 | 1.41 |
| | | | | Acoustic (ultrasonic) sensitivity [dB] | −72.2 | −71.5 | −73.1 | −72.9 | −73.0 | −71.8 | −71.2 |

| | | | | Exammple 15 | Exammple 16 | Exammple 17 | Exammple 18 | Exammple 19 | Exammple 20 | Example 21 |
|---|---|---|---|---|---|---|---|---|---|---|
| Mixture composition | Polysiloxane | Component (A) | Type | PDV-0541 | PDV-0541 | PDV-0541 | PDV-0541 | PDV-0541 | PDV-0541 | PDV-0541 |
| | | | Molecular weight | 60,000 | 60,000 | 60,000 | 60,000 | 60,000 | 60,000 | 60,000 |
| | | | Content [parts by mass] | 55.3 | 79.1 | 71.2 | 63.3 | 51.4 | 47.5 | 41.5 |
| | | Component (B) | Type | HMS-991 | HMS-991 | HMS-991 | HMS-991 | HMS-991 | HMS-991 | HMS-991 |
| | | | Molecular weight | 1,600 | 1,600 | 1,600 | 1,600 | 1,600 | 1,600 | 1,600 |
| | | | Equivalent [g/mol] | 67 | 67 | 67 | 67 | 67 | 67 | 67 |
| | | | Content [parts by mass] | 0.7 | 0.9 | 0.8 | 0.7 | 0.6 | 0.5 | 0.5 |
| | Zinc oxide | | Type | 25-LPT | 50S-LPT | 50S-LPT | 50S-LPT | 50S-LPT | 50S-LPT | 50S-LPT |
| | | | Average primary particle diameter [nm] | 60 | 20 | 20 | 20 | 20 | 20 | 20 |
| | | | Content [mass %] | 44.0 | 20.0 | 28.0 | 36.0 | 48.0 | 52.0 | 58.0 |
| Evaluation | | | JIS hardness | 40 | 36 | 40 | 41 | 42 | 43 | 45 |
| | | | Tear strength [N/cm] | 10 | 6 | 8 | 10 | 16 | 20 | 25 |
| | | | Taber abrasion amount [%] | 0.06 | 0.04 | 0.07 | 0.10 | 0.27 | 0.33 | 0.41 |
| | | | Acoustic impedance [×10$^4$ kg/m$^2$/sec] | 1.41 | 1.16 | 1.23 | 1.31 | 1.43 | 1.45 | 1.50 |
| | | | Acoustic (ultrasonic) sensitivity [dB] | −71.9 | −70.6 | −71.3 | −72.0 | −72.7 | −73.0 | −73.3 |

| | | | | Example 22 | Comparative Example 1 | Comparative Example 2 | Comparative Example 3 | Comparative Example 4 | Comparative Example 5 |
|---|---|---|---|---|---|---|---|---|---|
| Mixture composition | Polysiloxane | Component (A) | Type | PDV-0541 | DMS-V41 | DMS-V41 | DMS-V41 | PDV-0541 | DMS-V41 |
| | | | Molecular weight | 60,000 | 62,700 | 62,700 | 62,700 | 60,000 | 62,700 |
| | | | Content [parts by mass] | 37.6 | 59.0 | 59.3 | 49.5 | 98.9 | 55.3 |
| | | Component (B) | Type | HMS-991 | HMS-991 | HMS-991 | HMS-991 | HMS-991 | HMS-991 |
| | | | Molecular weight | 1,600 | 1,600 | 1,600 | 1,600 | 1,600 | 1,600 |
| | | | Equivalent [g/mol] | 67 | 67 | 67 | 67 | 67 | 67 |
| | | | Content [parts by mass] | 0.4 | 1.0 | 0.7 | 0.5 | 1.1 | 0.7 |
| | Zinc oxide | | Type | 50S-LPT | 30S-LPT | 30S-LPT | 30S-LPT | — | 50S-LPT |
| | | | Average primary particle diameter [nm] | 20 | 35 | 35 | 35 | — | 20 |
| | | | Content [mass %] | 62.0 | 10.0 | 40.0 | 50.0 | — | 44.0 |
| Evaluation | | | JIS hardness | 47 | 23 | 43 | 46 | 8 | 47 |
| | | | Tear strength [N/cm] | 37 | 2 | 16 | 28 | 1 | 32 |
| | | | Taber abrasion amount [%] | 0.48 | 0.02 | 0.51 | 0.62 | 0.01 | 0.56 |
| | | | Acoustic impedance [×10$^4$ kg/m$^2$/sec] | 1.54 | 1.10 | 1.24 | 1.36 | 1.10 | 1.33 |
| | | | Acoustic (ultrasonic) sensitivity [dB] | −73.7 | −65.7 | −72.1 | −72.9 | −63.5 | −72.4 |

<Notes of Table>
[Polysiloxane Component (A)]
All are PDV (trade name) and DMS (trade name) series manufactured by GELEST, INC.
PDV-0541: trade name, vinyl terminated diphenylsiloxane-dimethylsiloxane copolymer, mass average molecular weight of 60,000, diphenylsiloxane amount of 5 mol %
PDV-0535: trade name, vinyl terminated diphenylsiloxane-dimethylsiloxane copolymer, mass average molecular weight of 47,500, diphenylsiloxane amount of 5 mol %
PDV-1641: trade name, vinyl terminated diphenylsiloxane-dimethylsiloxane copolymer, mass average molecular weight of 55,000, diphenylsiloxane amount of 16 mol %
PDV-1635: trade name, vinyl terminated diphenylsiloxane-dimethylsiloxane copolymer, mass average molecular weight of 35,300, diphenylsiloxane amount of 16 mol %
PDV-1631: trade name, vinyl terminated diphenylsiloxane-dimethylsiloxane copolymer, mass average molecular weight of 19,000, diphenylsiloxane amount of 16 mol %
DMS-V41: trade name, vinyl terminated polydimethylsiloxane, mass average molecular weight of 62,700, Si—H equivalent of 67 g/mol
[Polysiloxane Component (B)]
HMS-991: trade name, methylhydrosiloxane polymer manufactured by GELEST, INC., mass average molecular weight of 1,600, Si—H equivalent of 67 g/mol
HPM-502: trade name, methylhydrosiloxane-phenylmethylsiloxane copolymer manufactured by GELEST, INC., mass average molecular weight of 4,500, Si—H equivalent of 165 g/mol
HMS-151: trade name, methylhydrosiloxane-dimethylsiloxane copolymer manufactured by GELEST, INC., mass average molecular weight of 2,000, Si—H equivalent of 490 g/mol
HMS-301: trade name, methylhydrosiloxane-dimethylsiloxane copolymer manufactured by GELEST, INC., mass average molecular weight of 2,000, Si—H equivalent of 245 g/mol
HMS-501: trade name, methylhydrosiloxane-dimethylsiloxane copolymer manufactured by GELEST, INC., mass average molecular weight of 1,100, Si—H equivalent of 135 g/mol
HMS-064: trade name, methylhydrosiloxane-dimethylsiloxane copolymer manufactured by GELEST, INC., mass average molecular weight of 60,000, Si—H equivalent of 1,240 g/mol
[Zinc Oxide]
All are FINEX (registered trademark) zinc oxide series manufactured by SAKAI CHEMICAL INDUSTRY CO., LTD., and will be abbreviated as "FINEX-" in the above-described tables.
FINEX-50S-LPT: trade name, average primary particle diameter of 20 nm, silicone surface treatment
FINEX-75: trade name, average primary particle diameter of 15 nm, without silicone surface treatment
FINEX-50S-LP2: trade name, average primary particle diameter of 20 nm, without silicone surface treatment
FINEX-50: trade name, average primary particle diameter of 20 nm, without silicone surface treatment
FINEX-30S-LPT: trade name, average primary particle diameter of 35 nm, silicone surface treatment
FINEX-30W-LP2: trade name, average primary particle diameter of 35 nm, silica/silicone surface treatment
FINEX-25-LPT: trade name, average primary particle diameter of 60 nm, silicone surface treatment As is clear from Table 1, in the silicone resins for an acoustic wave probe of Examples 1 to 22, the acoustic impedance is close to a living body and all of the acoustic (ultrasonic) sensitivities are greater than or equal to −74 dB. It can be seen that the acoustic attenuation is decreased due to the sensitivities greater than or equal to −74 dB. Furthermore, the silicone resins for an acoustic wave probe of Examples 1 to 22 have excellent hardness, rear strength, and abrasion resistance. On the other hand, all of the silicone resins for an acoustic wave probe of Comparative Examples 1 to 4 at least have insufficient tear strength or abrasion resistance.

From the results, it can be seen that the composition for an acoustic wave probe of the present invention is suitable for a medical member. In addition, it can be seen that the silicone resin of the present invention can also be suitably used in the acoustic lens and/or the acoustic matching layer of the acoustic wave probe, the acoustic wave measurement apparatus, and the ultrasound diagnostic apparatus. Particularly, the composition for an acoustic wave probe and the silicone resin for an acoustic wave probe can be suitably used in the ultrasound probe in which cMUT is used as an ultrasonic diagnostic transducer array, the photoacoustic wave measurement apparatus, and the ultrasound endoscope for the purpose of improving the sensitivity.

The present invention has been described using an embodiment thereof. However, it is considered that, unless otherwise specified, even the detailed description of the invention is not limited and is necessarily widely interpreted without departing from the gist and the range of the invention shown in the attached Claims.

EXPLANATION OF REFERENCES

1: acoustic lens.
2: acoustic matching layer
3: piezoelectric element layer
4: backing material
7: housing
9: cord
10: ultrasound probe

What is claimed is:

1. An acoustic wave probe comprising:
at least one selected from the group consisting of an acoustic lens and an acoustic matching layer which contain a silicone resin for an acoustic wave probe which is obtained by subjecting a composition for an acoustic wave probe comprising a polysiloxane mixture containing at least polysiloxane having a vinyl group and a phenyl group, polysiloxane having two or more Si—H groups in a molecular chain, and zinc oxide, to a vulcanization reaction.

2. An acoustic wave measurement apparatus comprising:
the acoustic wave probe according to claim 1.

3. An ultrasound diagnostic apparatus comprising:
the acoustic wave probe according to claim 1.

4. An ultrasound probe comprising:
a capacitive micromachined ultrasonic transducer; and
an acoustic lens containing a silicone resin for an acoustic wave probe which is obtained by subjecting a composition for an acoustic wave probe comprising a polysiloxane mixture containing at least polysiloxane having a vinyl group and a phenyl group, polysiloxane having two or more Si—H groups in a molecular chain, and zinc oxide, to a vulcanization reaction.

5. An ultrasound endoscope comprising:
an acoustic lens containing a silicone resin for an acoustic wave probe which is obtained by subjecting a composition for an acoustic wave probe comprising a polysiloxane mixture containing at least polysiloxane having a vinyl group and a phenyl group, polysiloxane having two or more Si—H groups in a molecular chain, and zinc oxide, to a vulcanization reaction.

* * * * *